(12) United States Patent
Kollgaard et al.

(10) Patent No.: US 9,255,909 B2
(45) Date of Patent: Feb. 9, 2016

(54) SURFACE VISUALIZATION SYSTEM FOR INDICATING INCONSISTENCIES

(75) Inventors: Jeffrey R. Kollgaard, Seattle, WA (US); Tyler Holmes, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 948 days.

(21) Appl. No.: 13/430,132

(22) Filed: Mar. 26, 2012

(65) Prior Publication Data
US 2013/0250719 A1 Sep. 26, 2013

(51) Int. Cl.
*G01N 27/06* (2006.01)
*G01N 29/06* (2006.01)
*G01N 29/22* (2006.01)
*G01N 29/265* (2006.01)
*G01N 27/90* (2006.01)
*G01N 29/04* (2006.01)

(52) U.S. Cl.
CPC .............. *G01N 29/069* (2013.01); *G01N 27/90* (2013.01); *G01N 29/043* (2013.01); *G01N 29/225* (2013.01); *G01N 29/226* (2013.01); *G01N 29/265* (2013.01); *G01N 2291/044* (2013.01); *G01N 2291/2694* (2013.01)

(58) Field of Classification Search
CPC .......... G01N 2291/044; G01N 29/265; G01N 29/226; G01N 2291/2693; G01N 2291/2694
USPC .................................................... 73/635–369
See application file for complete search history.

(56) References Cited

U.S. PATENT DOCUMENTS

| | | | | |
|---|---|---|---|---|
| 2,525,873 A | * | 10/1950 | De Lano, Jr. .......... | G01N 29/06 367/7 |
| 3,670,562 A | * | 6/1972 | Muto .................... | G01N 29/223 73/634 |
| 3,700,801 A | * | 10/1972 | Dougherty .............. | F41G 7/343 250/203.7 |
| 3,802,533 A | * | 4/1974 | Brenden ............... | A61B 8/0825 181/176 |
| 4,470,122 A | * | 9/1984 | Sarr ...................... | G01B 11/002 702/150 |
| 4,581,939 A | * | 4/1986 | Takahashi .......... | G01N 29/2418 356/432 |
| 4,866,614 A | * | 9/1989 | Tam .................... | G01N 29/0618 600/437 |

(Continued)

OTHER PUBLICATIONS

"Array Wheel Probe Specification Data Sheet, Revision 1.2", www.sonatest.com, Jul. 2009, 1 Page.

(Continued)

*Primary Examiner* — Ari M Diacou
(74) *Attorney, Agent, or Firm* — Yee & Associates, P.C.

(57) ABSTRACT

A method and apparatus for indicating an inconsistency. An apparatus comprises a platform, a location system, a transducer system, a projector system, and a data processing system. The platform is configured to move on a surface of an object. The location system is configured to generate location information for the platform on the surface of the object. The transducer system is configured to send signals into the object and receive a response to the signals. The projector system is configured to project an image onto the surface of the object. The data processing system is configured to generate the image using the response. An indication of an inconsistency in the image projected onto the surface of the object corresponds to a location of the inconsistency in the object. The data processing system is configured to control the projector system to project the image onto the surface of the object.

22 Claims, 13 Drawing Sheets

(56) References Cited

U.S. PATENT DOCUMENTS

| | | | | |
|---|---|---|---|---|
| 4,896,278 A * | 1/1990 | Grove | G01N 29/265 | |
| | | | 250/559.46 | |
| 4,995,320 A * | 2/1991 | Sato | B61B 13/04 | |
| | | | 104/118 | |
| 6,092,420 A * | 7/2000 | Kimura | G01N 29/043 | |
| | | | 73/599 | |
| 6,382,028 B1 * | 5/2002 | Wooh | G01N 29/043 | |
| | | | 73/602 | |
| 7,193,696 B2 | 3/2007 | Engelbart et al. | | |
| 7,360,427 B2 * | 4/2008 | Drinkwater | G01N 29/223 | |
| | | | 73/635 | |
| 7,454,973 B2 * | 11/2008 | Baba | G01N 29/043 | |
| | | | 600/443 | |
| 7,480,037 B2 | 1/2009 | Palmateer et al. | | |
| 8,087,298 B1 * | 1/2012 | DiMambro | G01N 29/226 | |
| | | | 73/629 | |
| 8,402,830 B2 * | 3/2013 | Kleinert | G01N 29/069 | |
| | | | 73/602 | |
| 8,453,509 B2 * | 6/2013 | Oberdorfer | G01N 29/069 | |
| | | | 73/632 | |
| 8,714,018 B2 * | 5/2014 | Oberdoerfer | G01N 29/069 | |
| | | | 73/602 | |
| 2006/0123912 A1 * | 6/2006 | Karasawa | G01N 29/043 | |
| | | | 73/602 | |
| 2006/0219013 A1 * | 10/2006 | Baba | G01N 29/043 | |
| | | | 73/618 | |
| 2007/0034313 A1 | 2/2007 | Engelbart et al. | | |
| 2007/0039390 A1 * | 2/2007 | Duncan | G01N 29/226 | |
| | | | 73/606 | |
| 2007/0051177 A1 * | 3/2007 | Gifford | G01N 29/043 | |
| | | | 73/620 | |
| 2007/0125189 A1 * | 6/2007 | Bossi | G01N 27/902 | |
| | | | 73/865.8 | |
| 2007/0157730 A1 * | 7/2007 | Ochiai | F22B 37/003 | |
| | | | 73/627 | |
| 2008/0055591 A1 | 3/2008 | Walton | | |
| 2008/0141777 A1 * | 6/2008 | Engelbart | G03B 29/00 | |
| | | | 73/618 | |
| 2009/0257643 A1 * | 10/2009 | Engelbart | G06T 11/00 | |
| | | | 382/141 | |
| 2011/0016979 A1 * | 1/2011 | Oberdorfer | G01N 29/069 | |
| | | | 73/632 | |
| 2011/0178727 A1 * | 7/2011 | Hafenrichter | G01M 5/0016 | |
| | | | 702/38 | |

OTHER PUBLICATIONS

Freeman et al., "Scanned Laser Pico-Projectors: Seeing the Big Picture (with a small device)", Optics & Photonics News, vol. 20 No. 5, May 2009, pp. 28-34.

Extended European Search Report, dated Nov. 6, 2015, regarding Applicatoin No. EP13161171.7, 6 pages.

* cited by examiner

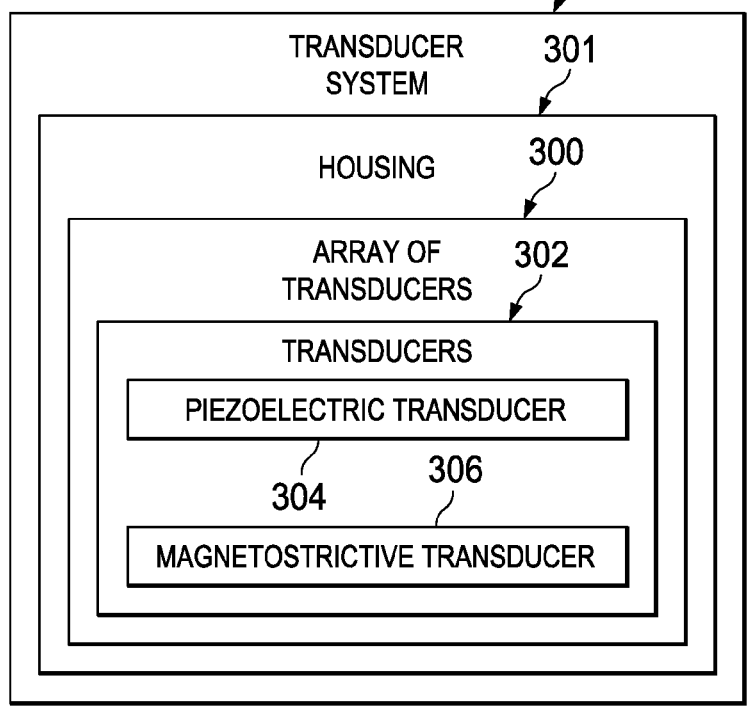
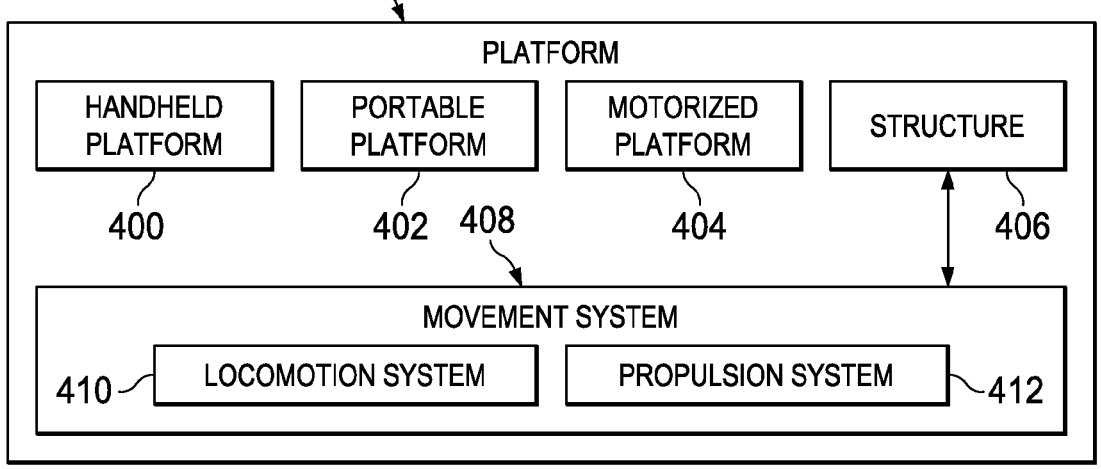

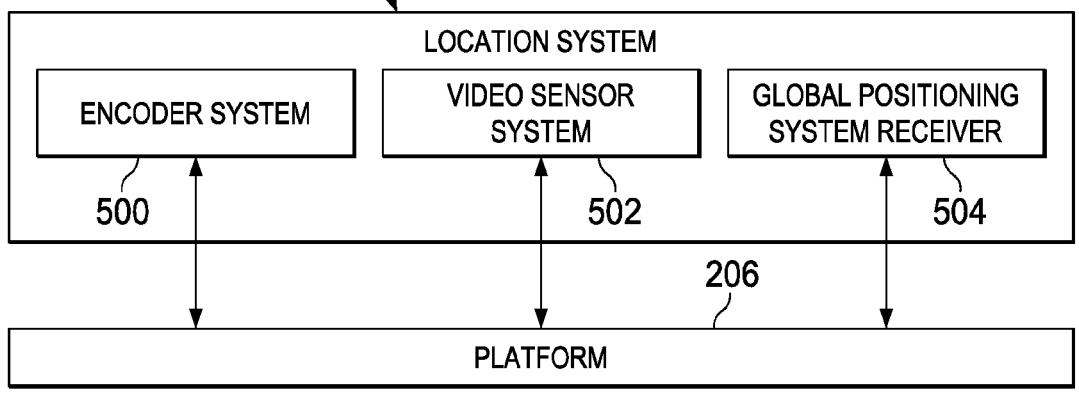
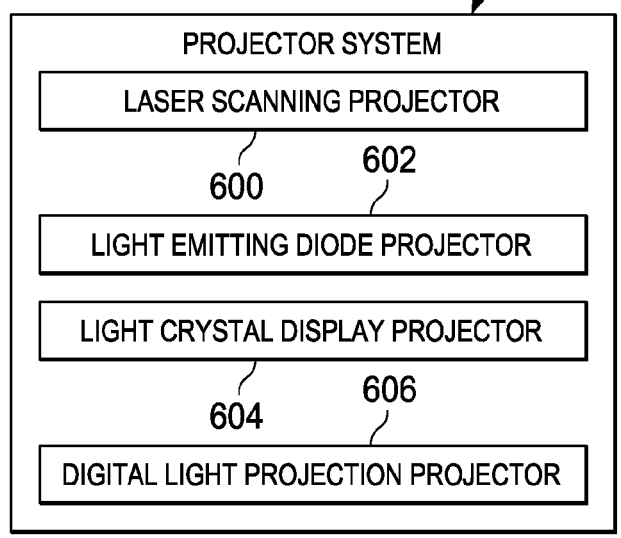

SURFACE VISUALIZATION SYSTEM FOR INDICATING INCONSISTENCIES

BACKGROUND INFORMATION

1. Field

The present disclosure relates generally to inspecting objects and, in particular, to identifying inconsistencies in objects. Still more particularly, the present disclosure relates to a method and apparatus for projecting an image of an inconsistency on the surface of an object in a location corresponding to the location of the inconsistency using a projector mounted on the end effector of the inspection device that does not rely on global coordinate systems.

2. Background

Nondestructive inspection involves different analysis techniques used to evaluate the properties of an object without causing damage to the object. Nondestructive inspection may be performed in a number of different ways. For example, nondestructive inspection may include ultrasonic testing. Ultrasonic testing involves using sound waves to inspect objects. The object tested may be comprised of different types of materials. For example, the materials may be one of steel, metals, alloys, concrete, wood, composite materials, and other types of materials.

With ultrasonic testing, transducers send first sound waves (pulses) into an object. Second sound waves (echoes) are received as a response to the first sound waves sent into the object. The response is analyzed for a number of different purposes. For example, the analysis may be used to characterize materials in the object, identify inconsistencies, and for other purposes.

Determining whether inconsistencies are present may be performed at different times during the life cycle of an object. For example, a nondestructive inspection may be made on an object after manufacturing the object, while the object is in use, during maintenance, and at other suitable times. The inspections often involve "C-scan" or spatial maps showing signal responses of interest in context of the structure. The C-scan may be displayed as images on a display device.

For example, ultrasonic inspection may be used to determine whether an inconsistency is present on an aircraft part. The aircraft part may be one that has been manufactured or is in use. Once an inconsistency is identified in the aircraft part, a determination may be made whether to rework the object, replace the object, or discard the object. Marking the location of the inconsistency is performed to assist in evaluation and rework.

With currently used ultrasonic inspection systems, marking the location of an inconsistency on the surface of the object may be more difficult than desired. Currently used sensor systems require the operator to accurately transfer the inconsistency shown in the external C-scan image to the surface of the object. The manual operations performed by the operator to transfer the location of the inconsistency for rework may take longer than desired and may not be as accurate as desired.

Therefore, it would be desirable to have a method and apparatus that takes into account one or more of the issues discussed above as well as possibly other issues.

SUMMARY

In one illustrative embodiment, an apparatus comprises a platform, a location system for the platform, a transducer system associated with the platform, a projector system associated with the platform, and a data processing system in communication with the transducer system and the projector system. The platform is configured to move on a surface of an object. The location system is configured to generate location information for the platform on the surface of the object. The transducer system is configured to send signals into the object and receive a response to the signals. The projector system is configured to project an image onto the surface of the object. The data processing system is configured to generate an image using the response. An indication of an inconsistency in the image projected onto the surface of the object corresponds to a location of the inconsistency in the object. The data processing system is further configured to control the projector system to project the image onto the surface of the object.

In another illustrative embodiment, an apparatus comprises a platform, a location system for the platform, a detection system associated with the platform, a projector system associated with the platform, and a data processing system in communication with the detection system and the projector system. The platform is configured to move on a surface of an object. The location system is configured to generate location information for the platform on the surface of the object. The detection system is configured to generate data about the object. The projector system is configured to project an image onto the surface of the object. The data processing system is configured to generate an image using the data from the detection system in which an indication of an inconsistency in the image projected onto the surface of the object corresponds to a location of the inconsistency in the object and control the projector system to project the image onto the surface of the object.

In yet another illustrative embodiment, a method for indicating an inconsistency is present. An image is generated using a response received from signals sent into an object from a transducer system in an ultrasonic inspection system. An indication of an inconsistency is present in the image. The image is projected onto a surface of the object from a projector in the ultrasonic inspection system. The indication of the inconsistency in the image corresponds to a location of the inconsistency in the object.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives, and features thereof will best be understood by reference to the following detailed description of an illustrative embodiment of the present disclosure when read in conjunction with the accompanying drawings, wherein:

FIG. 3 is an illustration of a block diagram of a transducer system in accordance with an illustrative embodiment;

FIG. 4 is an illustration of a block diagram of components for a platform in accordance with an illustrative embodiment;

FIG. 5 is an illustration of a block diagram of a location system in accordance with an illustrative embodiment;

FIG. 6 is an illustration of a block diagram of a projector system in accordance with an illustrative embodiment;

DETAILED DESCRIPTION

The illustrative embodiments recognize and take into account one or more different considerations. For example, the illustrative embodiments recognize and take into account that one difficulty in identifying the location of an inconsistency on an object involves the size of the ultrasonic sensor. Currently used ultrasonic sensor arrays have a size that blocks access to the surface in which the inconsistency has been located. In other words, the ultrasonic inspection unit with the array covers the surface of the object. When a response is received that indicates an inconsistency is present, the operator does not have access to the portion of the surface over which the array is located to mark the surface to indicate the presence of the inconsistency. In this case, the operator may use a smaller sensor to identify the location of an inconsistency after a larger sensor array has detected the presence of the inconsistency. This type of process requires additional time and effort and may take more time than needed to mark the locations of inconsistencies on an object.

The illustrative embodiments recognize and take into account that another solution may be to use the data generated by the sensor array to produce a transparency. This transparency indicates a location on which an inconsistency is present. More specifically, a hole is made in the transparency in the location where the inconsistency is present. The illustrative embodiments recognize and take into account that one solution involves generating a C-scan image that is true scale or that can be printed true scale.

An operator then correlates the indications of the inconsistencies on the transparency with the surface of the part. After the transparency has been laid on the surface of the object in a location, the inconsistency may then be marked using the hole in the transparency. Although using a transparency may identify locations of inconsistencies on an object with a desired level of accuracy, this type of process may be more expensive and take more time than desired. The illustrative embodiments recognize and take into account that access to a 1:1 true scale printer is seldom possible in the field. Further, the illustrative embodiments recognize and take into account that a C-scan image displayed on an ultrasonic scanning system does not have a 1:1 scale.

Figure 1:
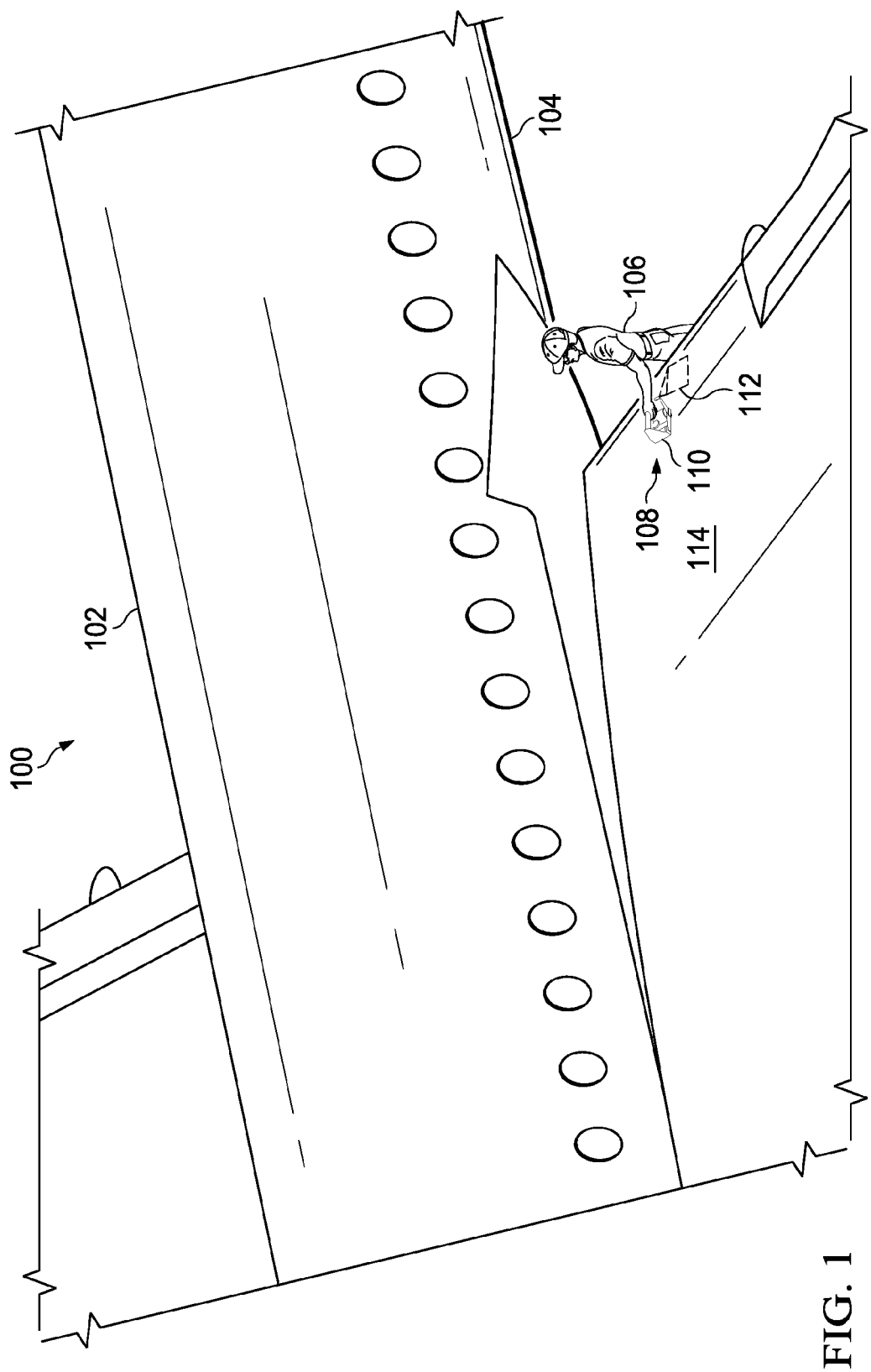
FIG. 1 is an illustration of an inspection environment in accordance with an illustrative embodiment.

With reference now to the figures and, in particular, with reference to FIG. 1, an illustration of an inspection environment is depicted in accordance with an illustrative embodiment. In this depicted example, inspection environment 100 includes object 102. As depicted, object 102 takes the form of aircraft 104.

In this illustrative example, operator 106 performs inspection of aircraft 104 using inspection system 108. In these illustrative examples, inspection system 108 takes the form of handheld ultrasonic inspection system 110.

As depicted, handheld ultrasonic inspection system 110 projects image 112 onto surface 114 of aircraft 104. In this illustrative example, operator 106 may then mark surface 114 based on image 112.

One solution recognized by the illustrative embodiments is that an additional inspection may be made. Locations of inconsistencies may be marked for rework. In some cases, the locations in which inconsistencies are marked on surface 114 may result in replacement of parts marked as having inconsistencies.

Figure 2:
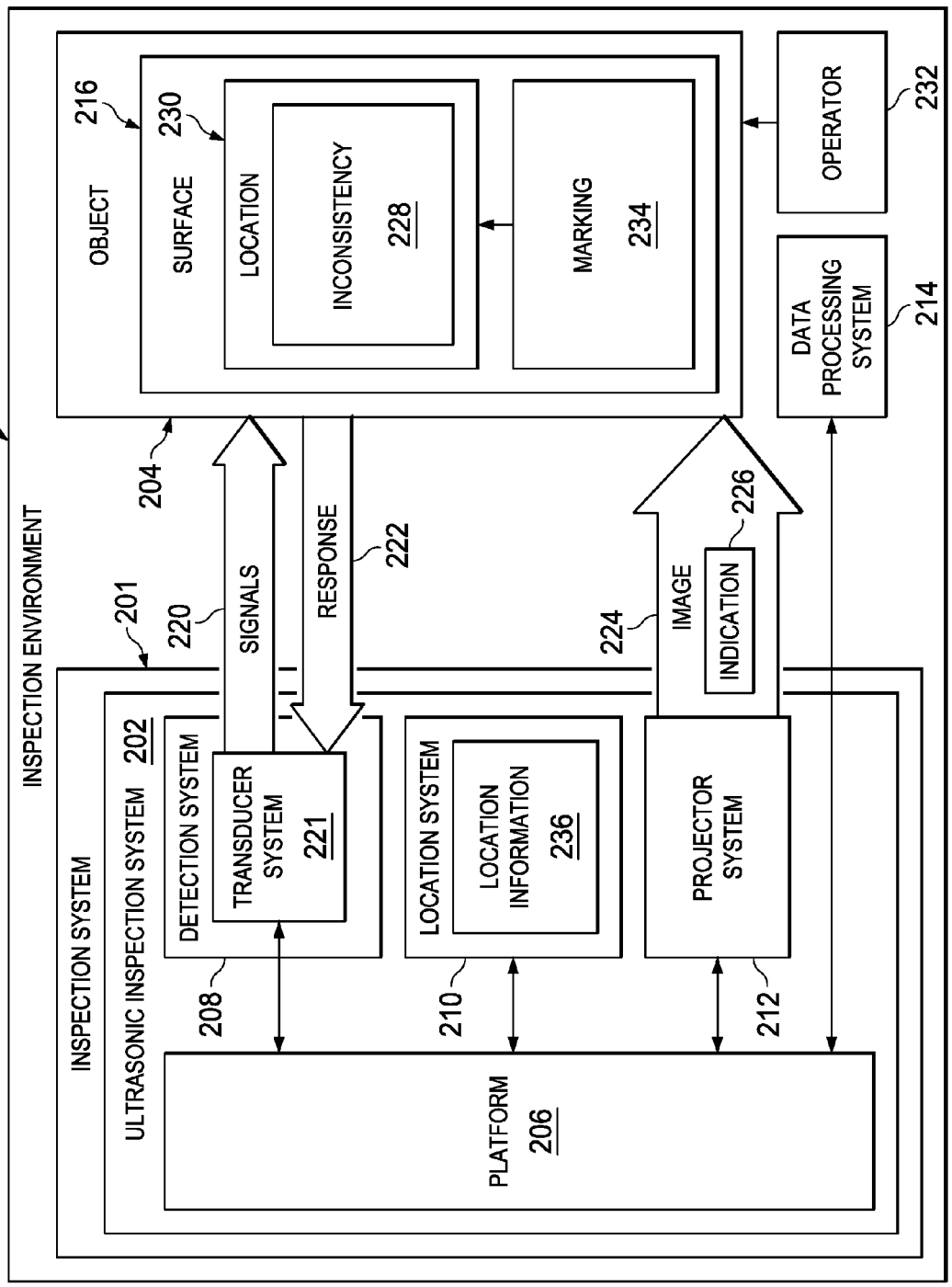
FIG. 2 is an illustration of a block diagram of an inspection environment in accordance with an illustrative embodiment.

Turning now to FIG. 2, an illustration of a block diagram of an inspection system is depicted in accordance with an illustrative embodiment. In this depicted example, inspection environment 100 in FIG. 1 is an example of one implementation for inspection environment 200.

In this illustrative example, inspection system 201 takes the form of ultrasonic inspection system 202 and is used to perform nondestructive inspection of object 204. In these illustrative examples, object 204 may take various forms, including aircraft 104 in FIG. 1.

Additionally, object 204 also may take other forms. For example, without limitation, object 204 may be selected from one of a mobile platform, a stationary platform, a land-based structure, an aquatic-based structure, a space-based structure, a submarine, a bus, a personnel carrier, a tank, a train, an automobile, a spacecraft, a space station, a satellite, a surface ship, an engine housing, a fuselage, a wing, a composite airfoil, a composite skin panel, a metal skin panel, a vertical stabilizer, a horizontal stabilizer, a joint, and/or some other suitable object.

In this illustrative example, ultrasonic inspection system 202 comprises platform 206, detection system 208, location system 210, projector system 212, and data processing system 214. Platform 206 is configured to move on surface 216 of object 204. In these illustrative examples, different components in platform 206 may be connected to data processing system 214 by wires or may use wireless transmission links.

Detection system 208 is associated with platform 206. Detection system 208 is configured to generate data about object 204. In this illustrative example, detection system 208 takes the form of transducer system 221 and is configured to send signals 220 into object 204 and receive response 222 to signals 220. Transducer system 221 is comprised of an array of transducers arranged in a line in this illustrative example.

When one component is "associated" with another component, the association is a physical association in these depicted examples. For example, a first component, such as transducer system 221, may be considered to be associated with a second component, such as platform 206, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component.

In these illustrative examples, response 222 also may take the form of signals. Signals 220 take the form of sound waves in these illustrative examples. The frequency of signals 220 transmitted by transducer system 221 may be, for example, from about 0.1 megahertz to about 50 megahertz, depending on the particular implementation.

Location system 210 is a hardware system for platform 206 and is comprised of hardware. Location system 210 may be associated with platform 206 or may be located remotely to platform 206 in these depicted examples. Location system 210 is configured to identify a location of platform 206 on surface 216 of object 204.

Location system 210 generates location information 236 about platform 206 on surface 216 of object 204. Location information 236 may be actual coordinates relative to object 204, a distance that platform 206 has moved, and/or some other suitable type of information.

Projector system 212 is a hardware device and is associated with platform 206 in this depicted example. Projector system 212 is configured to display image 224 on surface 216 of object 204. In particular, projector system 212 is configured to project light such that image 224 is projected onto surface 216 of object 204.

In these illustrative examples, data processing system 214 is in communication with transducer system 221, location system 210, and projector system 212. Data processing system 214 may be associated with platform 206 in this depicted example.

Data processing system 214 is configured to generate image 224 for projection onto surface 216. In these illustrative examples, image 224 takes the form of a C-scan image. Data processing system 214 generates image 224 using response 222 to signals 220. In these illustrative examples, indication 226 may be present in image 224 for inconsistency 228 in object 204.

Data processing system 214 is configured to control the projection of indication 226 in image 224 by projector system 212. Data processing system 214 sends image 224 to projector system 212.

In particular, data processing system 214 is configured to control the projection of indication 226 in image 224 by projector system 212 onto surface 216 corresponding to location 230 of inconsistency 228 in object 204. In other words, indication 226 in image 224 as projected onto surface 216 by projector system 212 is projected onto surface 216 at location 230 at which inconsistency 228 is located.

In the illustrative examples, image 224 is a true scale image. An image that is true scale is one in which the items in the image have the same dimensions as the actual items. For example, an indication of an area of resin in the image as displayed has the same dimensions as the actual area of resin. In other words, when the image is projected onto surface 216, indication 226 should correspond to inconsistency 228. For example, the dimensions of indication 226 should match the dimensions of inconsistency 228. The match should occur when indication 226 in image 224 as projected onto surface 216 is aligned with inconsistency 228.

Inconsistency 228 may be located on surface 216 at location 230 or below surface 216 at location 230 in these illustrative examples. In these illustrative examples, inconsistency 228 may take various forms, depending on the particular implementation. For example, if object 204 is comprised of composite materials, inconsistency 228 may be a delamination, a resin pocket, or some other type of inconsistency.

With the projection of image 224 with indication 226 onto surface 216, operator 232 may create marking 234 on surface 216 of object 204. As depicted, marking 234 is in location 230 using indication 226 in image 224 as projected onto surface 216 of object 204.

Further, data processing system 214 may be configured to generate an alert when a first amplitude in response 222 is greater than a second amplitude for an absence of inconsistency 228 by a selected amount. The second amplitude may be identified from a baseline of amplitudes present when inconsistencies are absent. The alert may be visual, audio, or a combination of the two.

In this manner, time and effort needed to identify and mark the location of an inconsistency using a first ultrasonic inspection system and then a smaller ultrasonic inspection system may be reduced. Further, the delay in time and expense needed for creating transparencies and aligning those transparencies with the surface of an object also may be reduced.

With reference next to FIG. 3, an illustration of a block diagram of a transducer system is depicted in accordance with an illustrative embodiment. In this illustrative example, transducer system 221 is comprised of array of transducers 300 located in housing 301. In this example, array of transducers 300 is arranged along a line. Transducers 302 in array of transducers 300 may be comprised of different types of transducers. For example, without limitation, transducers 302 may include at least one of piezoelectric transducer 304, magnetostrictive transducer 306, and other suitable types of transducers.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and 10 of item C; four of item B and seven of item C; and other suitable combinations.

With reference now to FIG. 4, an illustration of a block diagram of components for a platform is depicted in accordance with an illustrative embodiment. In this illustrative example, platform 206 may take various forms. For example, platform 206 may be selected from one of handheld platform 400, portable platform 402, motorized platform 404, and other suitable forms.

Handheld platform 400 is a platform that may be operated by one or two hands of operator 232 in FIG. 2. Portable platform 402 may be a platform moveable by operator 232 and/or more than one operator. Motorized platform 404 is a version of platform 206 that may move without force applied by operator 232.

In these illustrative examples, platform 206 includes structure 406 and movement system 408. Structure 406 may take various forms. For example, structure 406 may be a frame, a housing, or some other suitable structure. Structure 406 is configured to hold and/or support other components of ultrasonic inspection system 202 in FIG. 2.

Movement system 408 is configured to provide movement for platform 206 on surface 216 of object 204 in FIG. 2. For example, movement system 408 may include locomotion system 410. Locomotion system 410 may include one or more wheels, tracks, legs, low friction surfaces, or other devices or units that provide for movement of platform 206 on surface 216 of object 204. In these illustrative examples, the movement of platform 206 facilitated by locomotion system 410 may be performed by operator 232 applying force to platform 206.

In some illustrative examples, movement system 408 also may include propulsion system 412. Propulsion system 412 may be, for example, a motor configured to operate locomotion system 410.

Turning now to FIG. 5, an illustration of a block diagram of a location system is depicted in accordance with an illustrative embodiment. In this illustrative example, location system 210 may be implemented in a number of different ways.

Location system 210 may take various forms, such as, for example, at least one of encoder system 500, video sensor system 502, global positioning system receiver 504, and/or other suitable types of components.

As depicted, encoder system 500 is associated with platform 206. Encoder system 500 is configured to identify the distance that platform 206 moves. As a result, if platform 206 is placed in one location and moved by distance X, this information is identified using encoder system 500. Encoder system 500 measures the distance moved whether the distance is linear or has some other route.

Video sensor system 502 may also be used to generate location information about platform 206. Video sensor system 502 is an example of a location system for platform 206 that is not associated with platform 206. Video sensor system 502 may comprise one or more video cameras that are directed toward platform 206 while platform 206 moves on object 204 in FIG. 2.

Video sensor system 502 may generate information about the movement of platform 206 on surface 216 of object 204 in FIG. 2. This information may include, for example, without limitation, the distance moved, a location of platform 206 using coordinates, such as those for object 204, and other suitable types of information.

In these illustrative examples, location system 210 may use global positioning system receiver 504. Global positioning system receiver 504 is associated with platform 206. Global positioning system receiver 504 may generate information about the location of platform 206 on surface 216 of object 204.

Turning now to FIG. 6, an illustration of a block diagram of projector system 212 is depicted in accordance with an illustrative embodiment. As depicted, projector system 212 may take various forms. For example, without limitation, projector system 212 may take the form of laser scanning projector 600, light emitting diode projector 602, liquid crystal display (LCD) projector 604, digital light projection (DLP) projector 606, or some other suitable type of projector.

Figure 7:
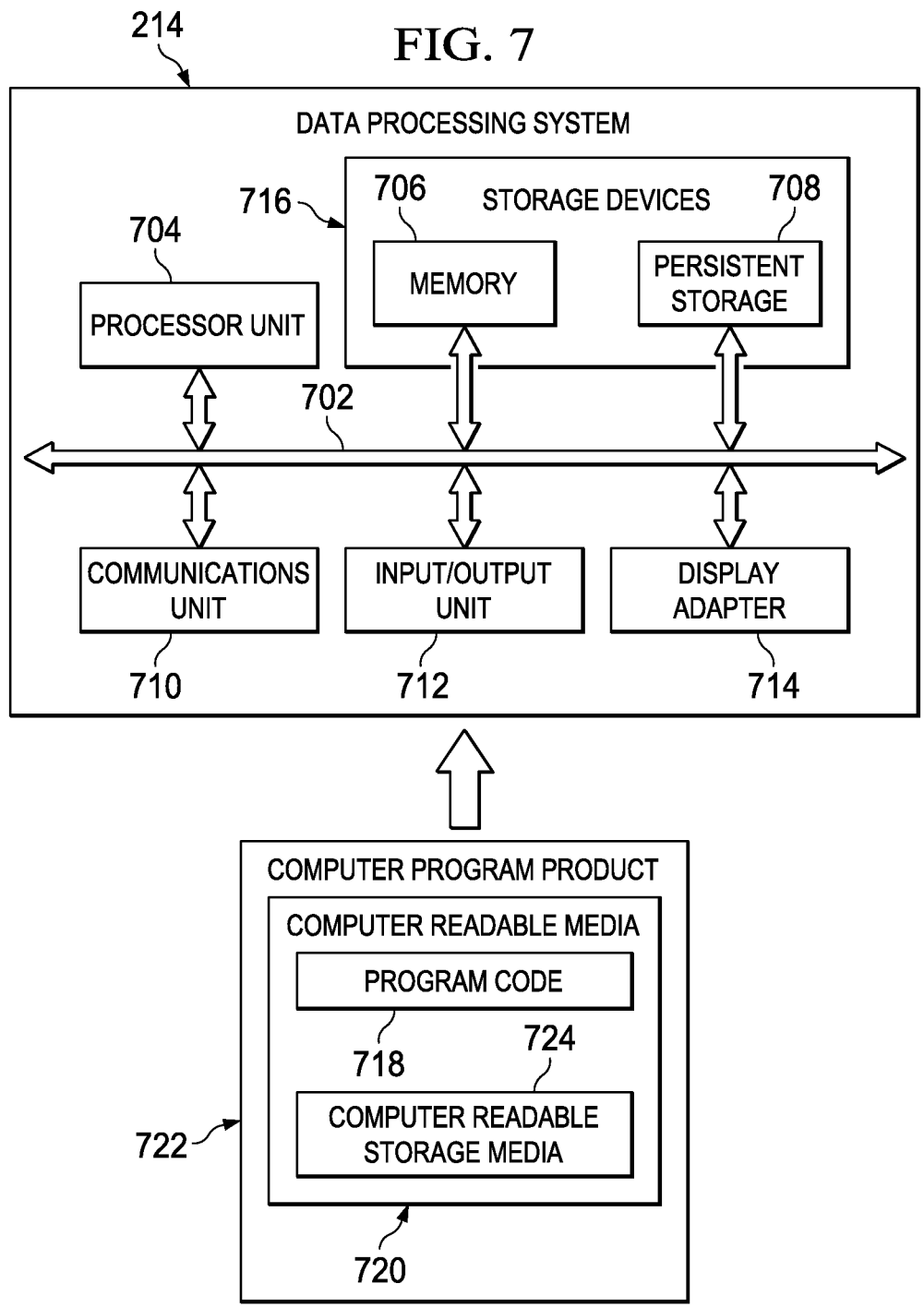
FIG. 7 is an illustration of a data processing system in accordance with an illustrative embodiment.

Turning now to FIG. 7, an illustration of a data processing system is depicted in accordance with an illustrative embodiment. An example of components that may be used to implement data processing system 214 is depicted. In this illustrative example, data processing system 214 includes communications framework 702, which provides communications between processor unit 704, memory 706, persistent storage 708, communications unit 710, input/output (I/O) unit 712, and display adapter 714. In this example, communications framework 702 may take the form of a bus system.

Processor unit 704 serves to execute instructions for software that may be loaded into memory 706. Processor unit 704 may be a number of processors, a multi-processor core, or some other type of processor, depending on the particular implementation.

Memory 706 and persistent storage 708 are examples of storage devices 716. A storage device is any piece of hardware that is capable of storing information, such as, for example, without limitation, data, program code in functional form, and/or other suitable information either on a temporary basis and/or a permanent basis. Storage devices 716 may also be referred to as computer readable storage devices in these illustrative examples. Memory 706, in these examples, may be, for example, a random access memory or any other suitable volatile or non-volatile storage device. Persistent storage 708 may take various forms, depending on the particular implementation.

For example, persistent storage 708 may contain one or more components or devices. For example, persistent storage 708 may be a hard drive, a flash memory, a rewritable optical disk, or some combination of the above.

Communications unit 710, in these illustrative examples, provides for communications with other data processing systems or devices. In these illustrative examples, communications unit 710 is a network interface card.

Input/output unit 712 allows for input and output of data with other devices that may be connected to data processing system 214. Display adapter 714 provides a mechanism to display information using a display device, such as projector system 212 in FIG. 2.

Instructions for the operating system, applications, and/or programs may be located in storage devices 716, which are in communication with processor unit 704 through communications framework 702. The processes of the different embodiments may be performed by processor unit 704 using computer-implemented instructions, which may be located in a memory, such as memory 706.

These instructions are referred to as program code, computer usable program code, or computer readable program code that may be read and executed by a processor in processor unit 704. The program code in the different embodiments may be embodied on different physical or computer readable storage media, such as memory 706 or persistent storage 708.

Program code 718 is located in a functional form on computer readable media 720 that is selectively removable and may be loaded onto or transferred to data processing system 214 for execution by processor unit 704. Program code 718 and computer readable media 720 form computer program product 722 in these illustrative examples. In one example, computer readable media 720 is computer readable storage media 724.

In these illustrative examples, computer readable storage media 724 is a physical or tangible storage device used to store program code 718 rather than a medium that propagates or transmits program code 718. Alternatively, program code 718 may be transferred to data processing system 214 over a wireless communications link.

The different components illustrated for data processing system 214 are not meant to provide architectural limitations to the manner in which different embodiments may be implemented. The different illustrative embodiments may be implemented in a data processing system including components in addition to and/or in place of those illustrated for data processing system 214. Other components shown in FIG. 7 can be varied from the illustrative examples shown. The different embodiments may be implemented using any hardware device or system capable of running program code 718.

The illustration of inspection environment 200 in FIG. 2 is a component used in inspection environment 200 in FIGS. 3-7 and is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although inspection system 201 has been described as ultrasonic inspection system 202 in one illustrative embodiment, inspection system 201 may be implemented using other types of nondestructive inspection devices other than ultrasonic transducers. For example, an eddy current testing system with eddy current arrays may be used in place of or in addition to ultrasonic arrays in transducer system 221.

Figure 8:
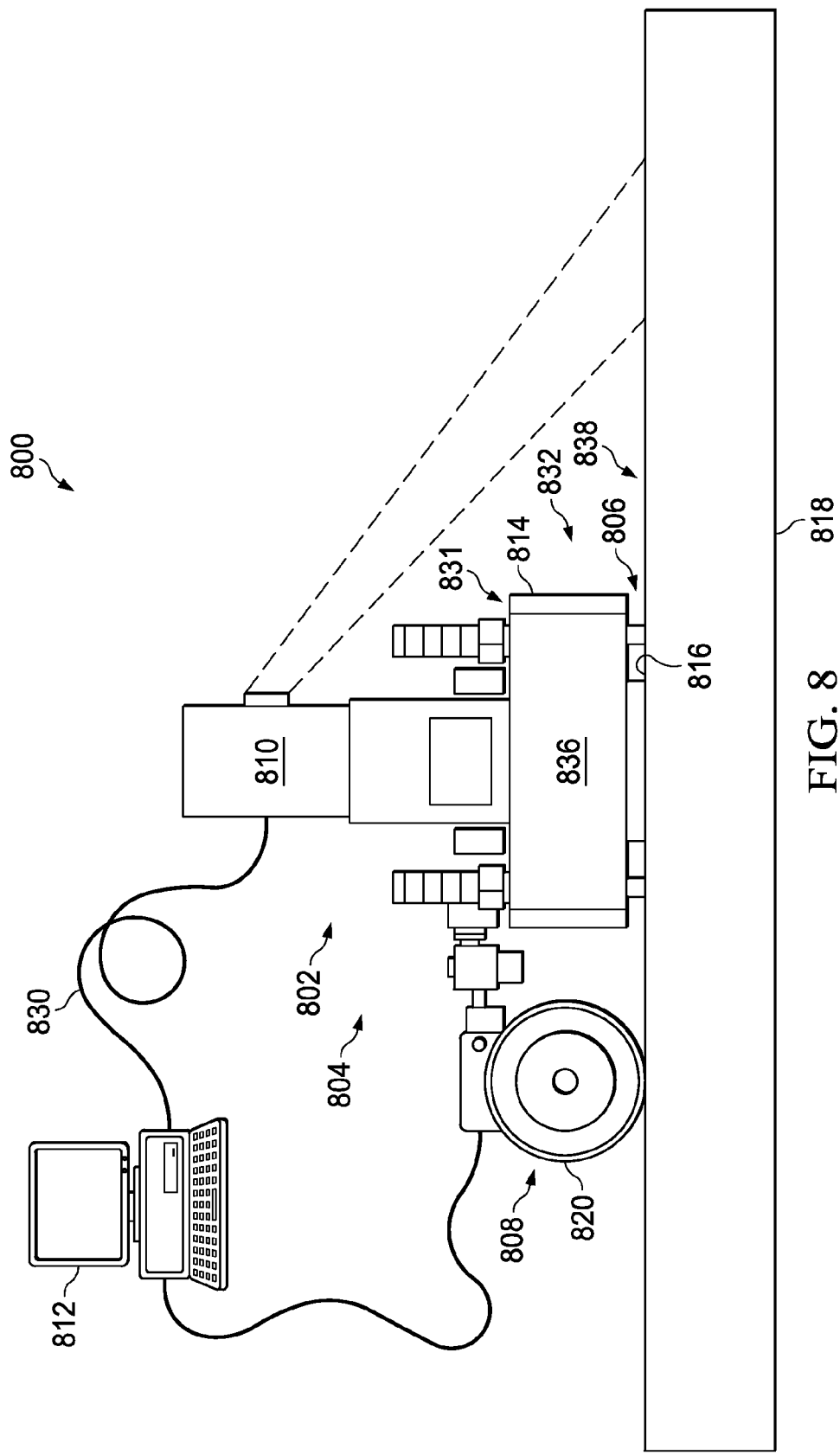
FIG. 8 is an illustration of an ultrasonic inspection system on the surface of an object in accordance with an illustrative embodiment.

Turning now to FIG. 8, an illustration of an ultrasonic inspection system on the surface of an object is depicted in accordance with an illustrative embodiment. In this depicted example, ultrasonic inspection system 800 is an example of another physical implementation of ultrasonic inspection system 202 shown in block form in FIG. 2.

In this illustrative example, ultrasonic inspection system 800 comprises platform 802. Platform 802 takes the form of handheld platform 804 in this illustrative example. As depicted, platform 802 comprises structure 831 and locomotion system 832. In this illustrative example, structure 831 takes the form of housing 836. Locomotion system 832 takes the form of low friction surface 838. In this illustrative example, transducer system 806, location system 808, and projector system 810 are associated with platform 802. Data processing system 812 is also present in ultrasonic inspection system 800.

In this illustrative example, transducer system 806 takes the form of an array of piezoelectric transducers located within housing 814. Housing 814 is configured to move over surface 816 of object 818.

As depicted, location system 808 takes the form of encoder 820. Encoder 820 is configured to generate information about a distance moved by ultrasonic inspection system 800.

Data processing system 812 is a computer system that is in communication with encoder 820, transducer system 806, and projector system 810. In this depicted example, data processing system 812 is not connected to platform 802. Instead, wires 830 connect data processing system 812 to transducer system 806, encoder 820, and projector system 810.

Figure 9:
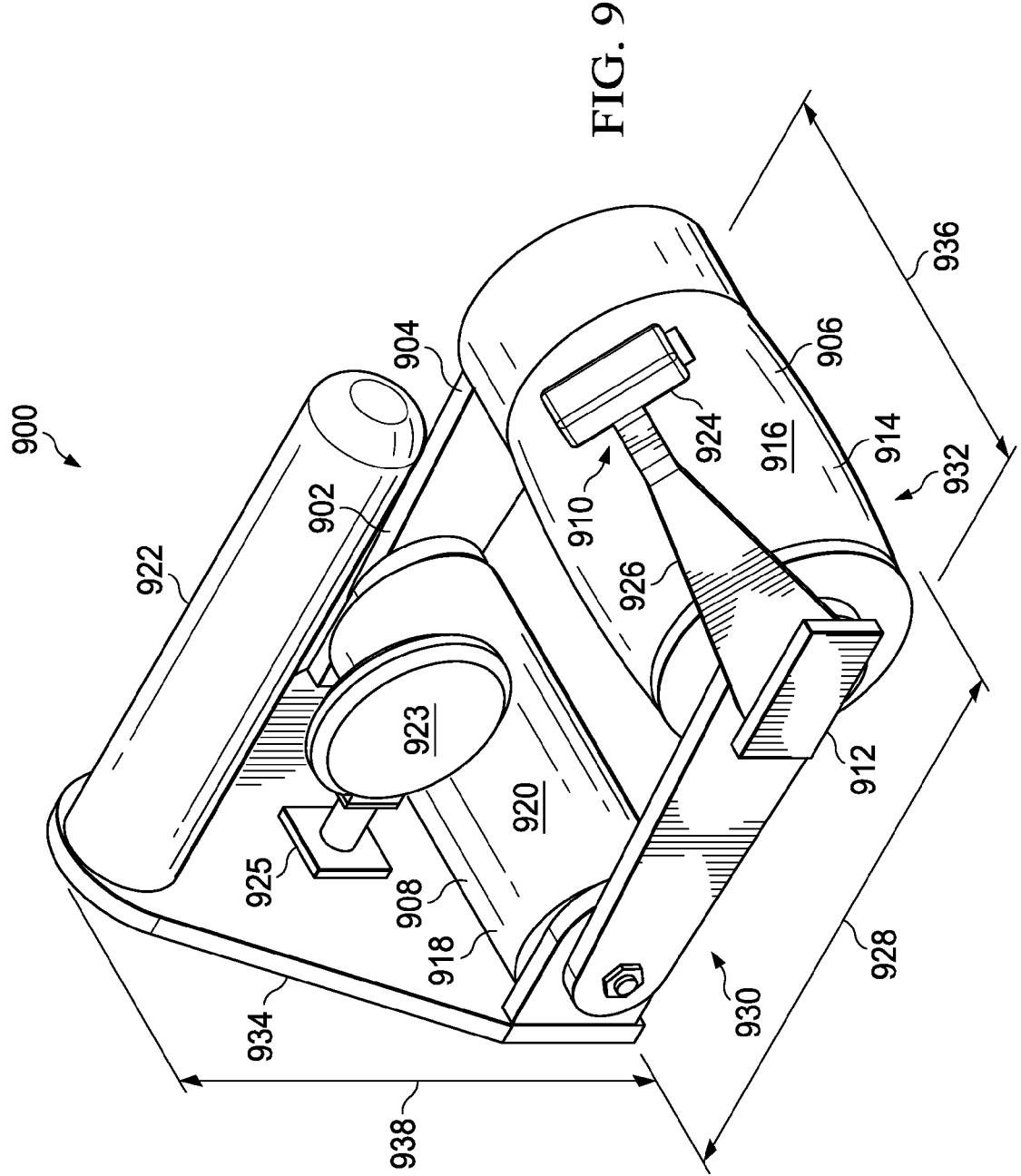
FIG. 9 is another illustration of an ultrasonic inspection system in accordance with an illustrative embodiment.

Turning now to FIG. 9, another illustration of an ultrasonic inspection system is depicted in accordance with an illustrative embodiment. In this illustrative example, ultrasonic inspection system 900 is an example of one physical implementation of ultrasonic inspection system 202 shown in block form in FIG. 2.

In this illustrative example, ultrasonic inspection system 900 comprises platform 902. In this illustrative example, platform 902 takes the form of handheld platform 904. In this illustrative example, platform 902 comprises structure 930 and movement system 932. Structure 930 takes the form of frame 934. Movement system 932 comprises roller 916 and roller 920.

In this illustrative example, handheld platform 904 also includes handle 922. Handle 922 has a size and shape configured to be held by the hand of a human operator. Handle 922 may be used to apply force to handheld platform 904 by an operator to move handheld platform 904.

Other components in ultrasonic inspection system 900 include transducer system 906, location system 908, projector system 910, and data processing system 912. As depicted, transducer system 906, location system 908, projector system 910, and data processing system 912 are components associated with platform 902.

As depicted, transducer system 906 takes the form of an array of piezoelectric transducers located inside of cylindrical housing 914. Cylindrical housing 914 may be rigid or deformable in these illustrative examples. Cylindrical housing 914 may be comprised of one or more materials that are conducive to the transmission of signals generated by the array of piezoelectric transducers within cylindrical housing 914. A coupling fluid may be present within cylindrical housing 914.

In this illustrative example, cylindrical housing 914 also forms roller 916. Roller 916 also may be part of a locomotion system for moving platform 902 on a surface of an object that is to be inspected.

Additionally, location system 908 takes the form of encoder 918, which includes roller 920. Roller 920 is another component that may be part of a locomotion system for platform 902 to aid in moving platform 902 on the surface of an object. In other illustrative examples, encoder 918 may be encoder wheel 923 that is in contact with roller 920. As encoder wheel 923 turns, the location information about the distance traveled by platform 902 is generated by encoder circuit 925.

Encoder 918 is configured to generate location information for ultrasonic inspection system 900. In particular, encoder 918 generates location information in the form of a distance moved by ultrasonic inspection system 900.

Transducer system 906 is configured to send signals into the surface of an object. Transducer system 906 is also configured to receive responses to those signals.

Data processing system 912 takes the form of a processor unit in these illustrative examples. Data processing system 912 also may include a memory, a storage device, and other suitable components, depending on the particular implementation.

Projector system 910 comprises projector 924. In this illustrative example, projector 924 takes the form of a laser scanning projector. Projector 924 is mounted on arm 926 extending from platform 902.

In operation, transducer system 906 sends signals into the surface of an object and receives a response to the signals sent into the object. Transducer system 906 may continuously or periodically send signals to the object as ultrasonic inspection system 900 is moved along the surface of the object. In this manner, multiple responses to the different signals are received. The responses are sent to data processing system 912. Further, as platform 902 is moved on the surface of an object, encoder 918 generates location information in the form of distance travelled by platform 902. This location information also is sent to data processing system 912.

In these illustrative examples, data processing system 912 uses the response from each set of signals sent into the object to generate an image. This image takes the form of a C-scan in these illustrative examples. The image may have different colors or gray scales, depending on the response received from the signals. The image is projected onto the surface of the object. The manner in which the image is projected onto the surface of the object is also performed using the location information from encoder 918. The location information is used to identify positions along an x-axis for the image for data generated by transducer system 906. The y-axis information is provided by the array of transducers within cylindrical housing 914 in these illustrative examples.

As depicted, ultrasonic inspection system 900 has length 928, width 936, and height 938. When platform 902 for ultrasonic inspection system 900 takes the form of handheld platform 904, ultrasonic inspection system 900 may have dimensions suitable for use by a single human operator. For example, length 928 may be about 11.5 inches, width 936 may be about 5.5 inches, and height 938 may be about 8 inches.

Figure 10:
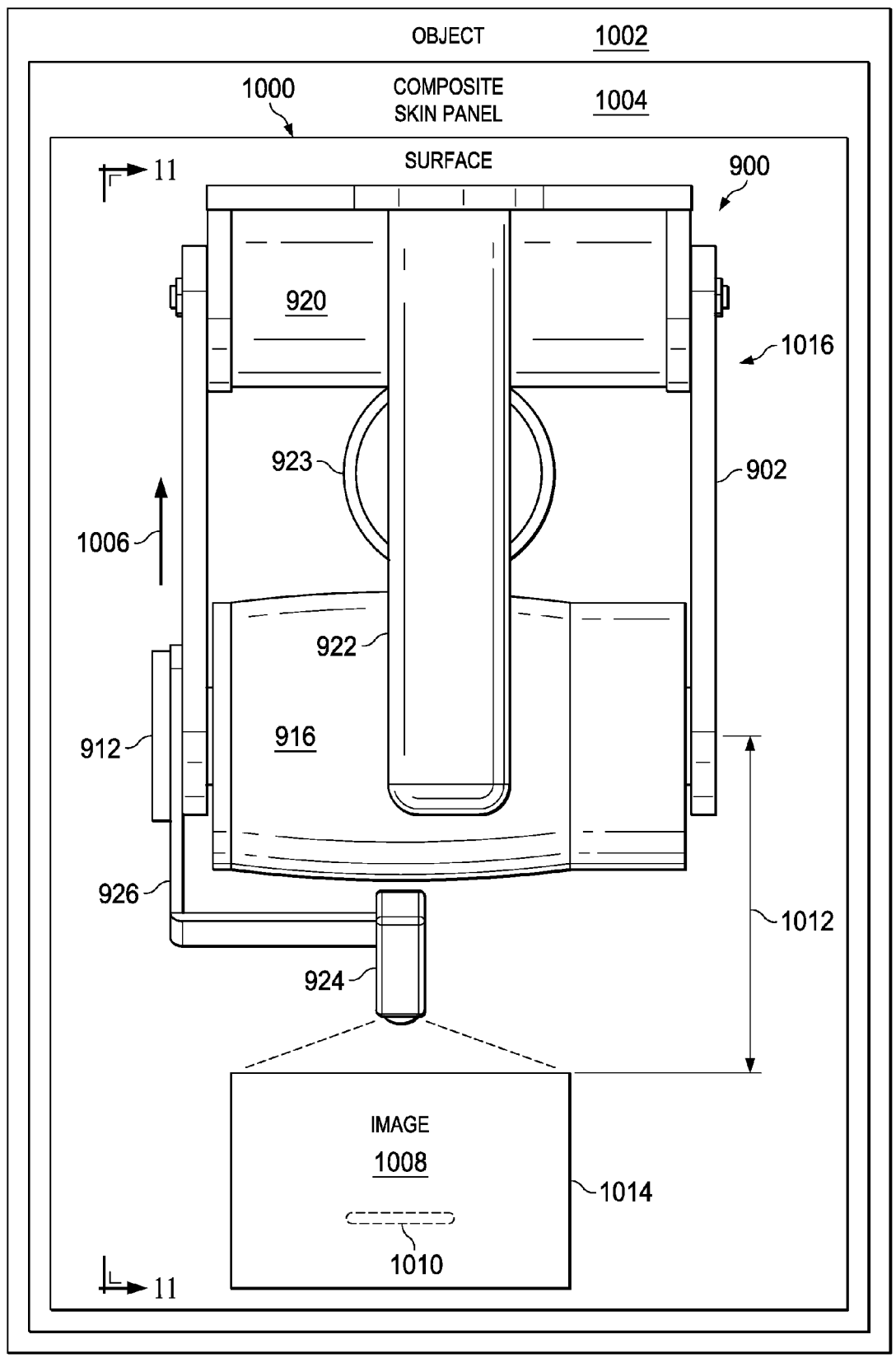
FIG. 10 is an illustration of an ultrasonic inspection system on a surface of an object in accordance with an illustrative embodiment.

Turning now to FIG. 10, an illustration of an ultrasonic inspection system on a surface of an object is depicted in accordance with an illustrative embodiment. In this depicted example, a top view of ultrasonic inspection system 900 is shown.

As depicted, ultrasonic inspection system 900 is located on surface 1000. In this illustrative example, object 1002 takes the form of composite skin panel 1004. Composite skin panel 1004 may be a part that has been manufactured or a part installed on an aircraft in this illustrative example.

As depicted, ultrasonic inspection system 900 is moved in the direction of arrow 1006. Image 1008 is projected by projector system 910 in FIG. 9 behind ultrasonic inspection system 900. The projection of image 1008 may occur while ultrasonic inspection system 900 is moved in the direction of arrow 1006. Additionally, image 1008 also may be projected while ultrasonic inspection system 900 is stationary.

In this illustrative example, indication 1010 is present in image 1008. Indication 1010 is an indication of an inconsistency in object 1002. In these illustrative examples, image 1008 is projected onto surface 1000 of object 1002 with a scale of one to one. In this manner, indication 1010 may have a size and shape that corresponds directly with the inconsistency. In other words, indication 1010, as shown in image 1008, has the same size and shape as the inconsistency in object 1002.

As depicted, image 1008 is displayed with offset 1012 from the array of transducers within cylindrical housing 914 in transducer system 906 in FIG. 9. In this illustrative example, offset 1012 along with location information from location system 908 in FIG. 9 may be used to generate and change image 1008 such that indication 1010 is displayed on surface 1000 of object 1002 in the location corresponding to the inconsistency detected by ultrasonic inspection system 900. In this illustrative example, offset 1012 is a distance from the array of transducers in cylindrical housing 914 to leading edge 1014 of image 1008.

For example, if offset 1012 is about two inches, information detected by the array in cylindrical housing 914 in location 1016 is not immediately displayed in image 1008. This information is displayed when the array of transducers moves about two inches in the direction of arrow 1006. In other words, an inconsistency detected by the array of transducers is not displayed in image 1008 until the array of transducers moves a distance that is substantially equal to offset 1012.

Figure 11:
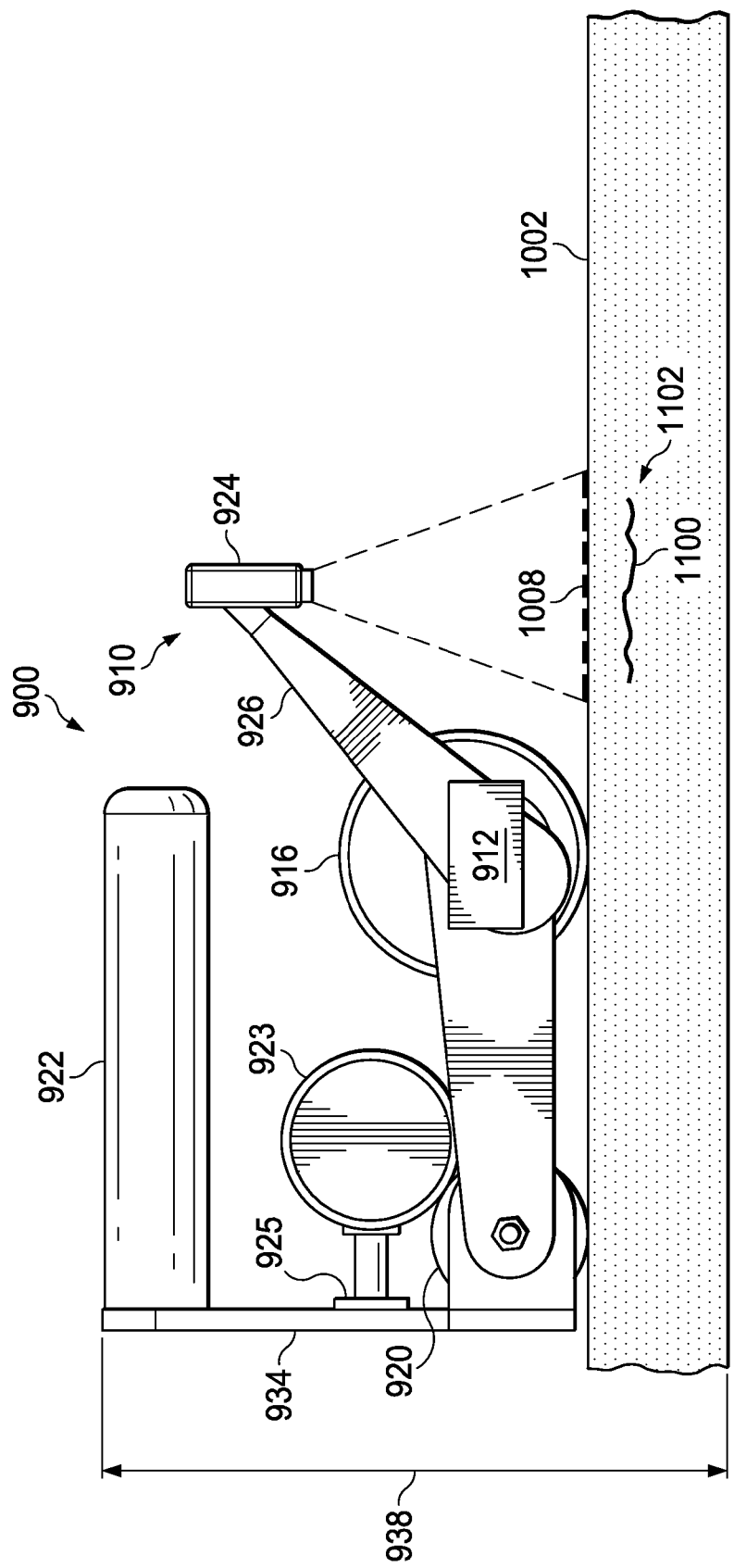
FIG. 11 is an illustration of a cross section of an object with an image projected onto the surface of the object in accordance with an illustrative embodiment.

Turning now to FIG. 11, an illustration of a cross section of an object with an image projected onto the surface of the object is depicted in accordance with an illustrative embodiment. In this depicted example, a cross-sectional view of a portion of object 1002 taken along lines 11-11 in FIG. 10 is shown. In this illustrative example, inconsistency 1100 can be seen within location 1102 within object 1002.

Figure 12:
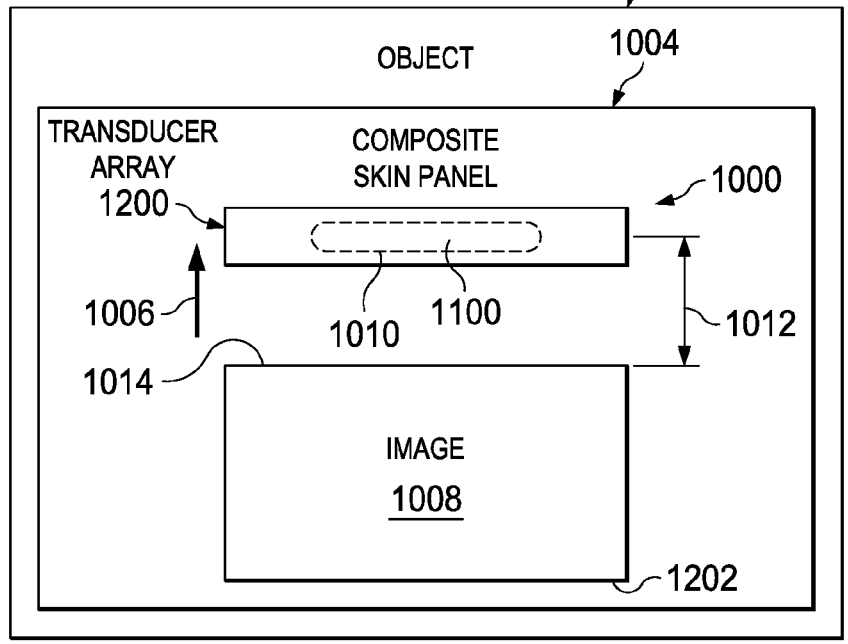
FIG. 12 is an illustration of a transducer array and an image projected on the surface of an object in accordance with an illustrative embodiment.

Turning now to FIG. 12, an illustration of a transducer array and an image projected on the surface of an object is depicted in accordance with an illustrative embodiment. In this depicted example, transducer array 1200 is an example of a transducer array that may be within transducer system 906 in FIG. 9, transducer system 806 in FIG. 8, or both transducer system 906 and transducer system 806.

In this illustrative example, transducer array 1200 is located over inconsistency 1100. As transducer array 1200 sends signals into object 1002, responses are received that indicate the presence of inconsistency 1100. Image 1008 is projected in a manner that illustrates information about object 1002 in which information in image 1008 corresponds to the responses received over the locations where the responses were received. As a result, an indication of the inconsistency is not shown in image 1008 in this example. Instead, image 1008 reflects information generated while transducer array 1200 is located over inconsistency 1100. In this illustrative example, indication 1010 shifts from leading edge 1014 toward trailing edge 1202 of image 1008. The information is displayed at leading edge 1014 after transducer array 1200 moves a distance in the direction of arrow 1006 by offset 1012.

In this example, transducer array 1200 is located over inconsistency 1100. As a result, information about inconsistency 1100 is not currently depicted in image 1008. This information is not shown until transducer array 1200 has been moved by the distance of offset 1012. As transducer array 1200 is moved in the direction of arrow 1006, image 1008 is changed to reflect information corresponding to locations where image 1008 is displayed.

Figure 13:
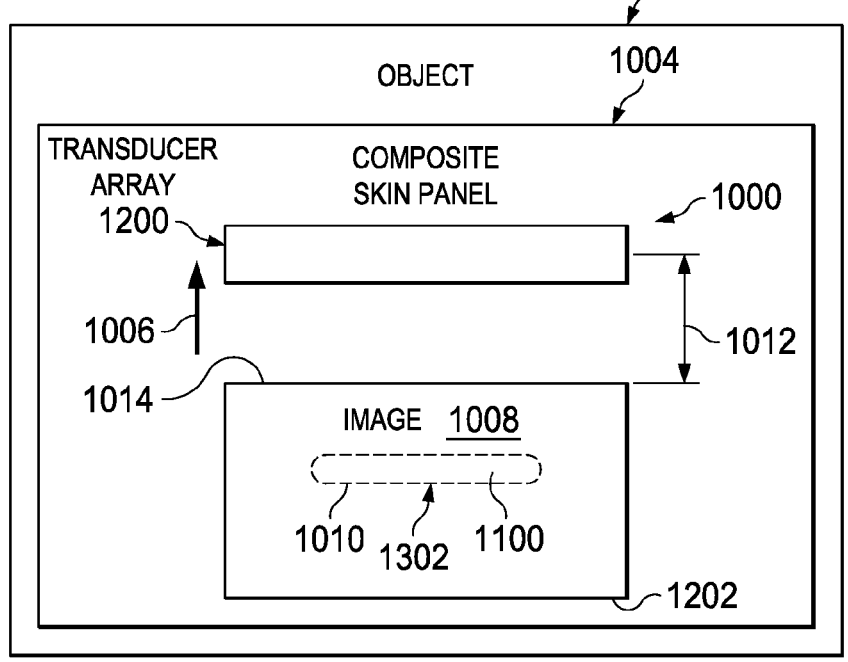
FIG. 13 is an illustration of a transducer array in accordance with an illustrative embodiment.

Turning now to FIG. 13, an illustration of a transducer array is depicted in accordance with an illustrative embodiment. Transducer array 1200 has moved further in the direction of arrow 1006. In this example, image 1008 is now displayed to show indication 1010 of inconsistency 1100 at leading edge 1014 of image 1008. Transducer array 1200 is moved further in the direction of arrow 1006, and image 1008 is again adjusted to show indication 1010 in location 1302 of inconsistency 1100 in its current position on surface 1000 of object 1002.

Figure 14:
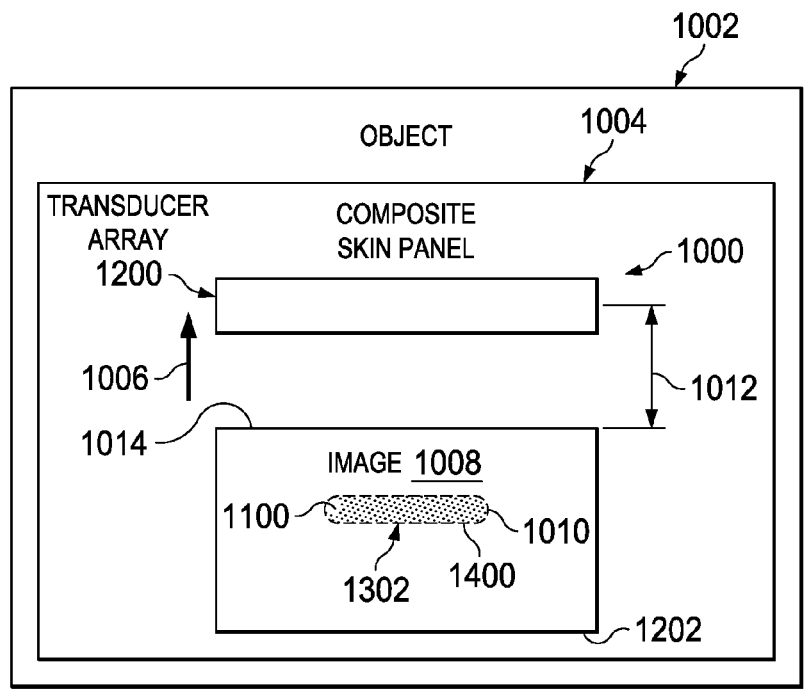
FIG. 14 is an illustration of a transducer array in an image in accordance with an illustrative embodiment.

With reference now to FIG. 14, an illustration of a transducer array in an image is depicted in accordance with an illustrative embodiment. In this illustrative example, transducer array 1200 has moved further in the direction of arrow 1006. With this movement, image 1008 is generated such that indication 1010 is now located closer toward trailing edge 1202 instead of leading edge 1014. In this manner, indication 1010 continues to shift toward trailing edge 1202 of image 1008 as transducer array 1200 moves in the direction of arrow 1006. This adjustment of indication 1010 is performed such that indication 1010 continues to be displayed on surface 1000 and location 1302 of inconsistency 1100.

As can be seen, indication 1010 shifts within image 1008 such that indication 1010 remains located over inconsistency 1100 within object 1002. With this type of projection, an operator may, without interference from transducer array 1200, mark surface 1000 of object 1002 with marker 1400 to indicate the presence of inconsistency 1100 in object 1002. In this manner, marker 1400 may be placed in a more accurate manner to indicate location 1302 of inconsistency 1100.

The different components shown in FIGS. 1 and 8-14 may be combined with components in FIGS. 2-7, used with components in FIGS. 2-7, or a combination of the two. Additionally, some of the components in FIGS. 1 and 8-14 may be illustrative examples of how components shown in block form in FIGS. 1 and 8-14 may be implemented as physical structures.

Figure 15:
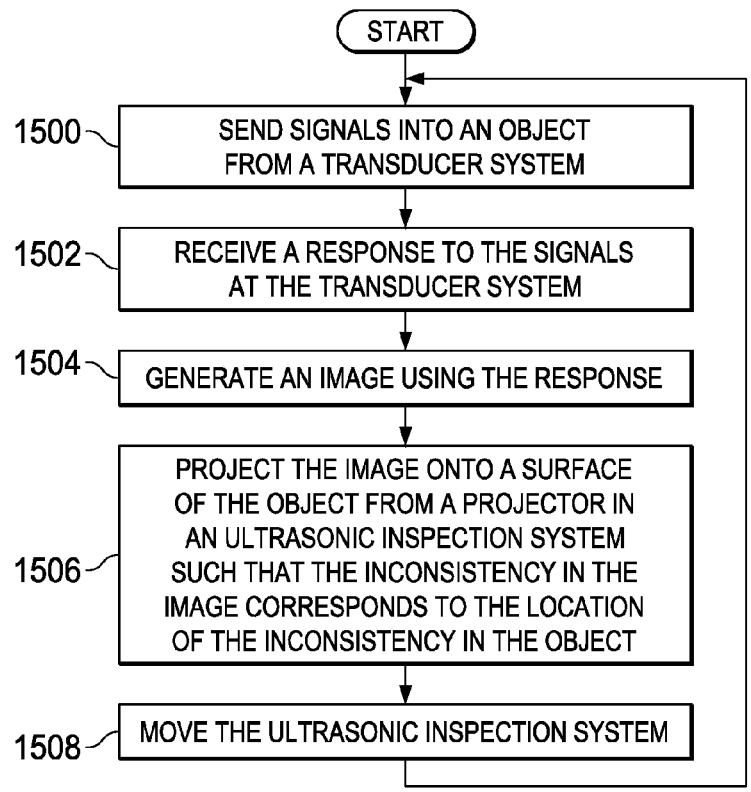
FIG. 15 is an illustration of a flowchart of a process for indicating a presence of an inconsistency in an object in accordance with an illustrative embodiment.

With reference now to FIG. 15, an illustration of a flowchart of a process for indicating a presence of an inconsistency in an object is depicted in accordance with an illustrative embodiment. The process illustrated in FIG. 15 may be implemented in an ultrasonic inspection system, such as ultrasonic inspection system 202 in FIG. 2.

The process begins by sending signals into an object from a transducer system (operation 1500). The process receives a response to the signals at the transducer system (operation 1502). The process then generates an image using the response (operation 1504). This image includes previous responses detected by the transducer system. The image is generated such that an indication of an inconsistency in the image corresponds to the location of the inconsistency in the object when the image is projected onto the surface of the object.

The process then projects the image onto a surface of the object from a projector in an ultrasonic inspection system such that the inconsistency in the image corresponds to the location of the inconsistency in the object (operation 1506).

The process then moves the ultrasonic inspection system (operation 1508), with the process then returning to operation 1500. These operations may be repeated as often as needed to inspect an object.

Figure 16:
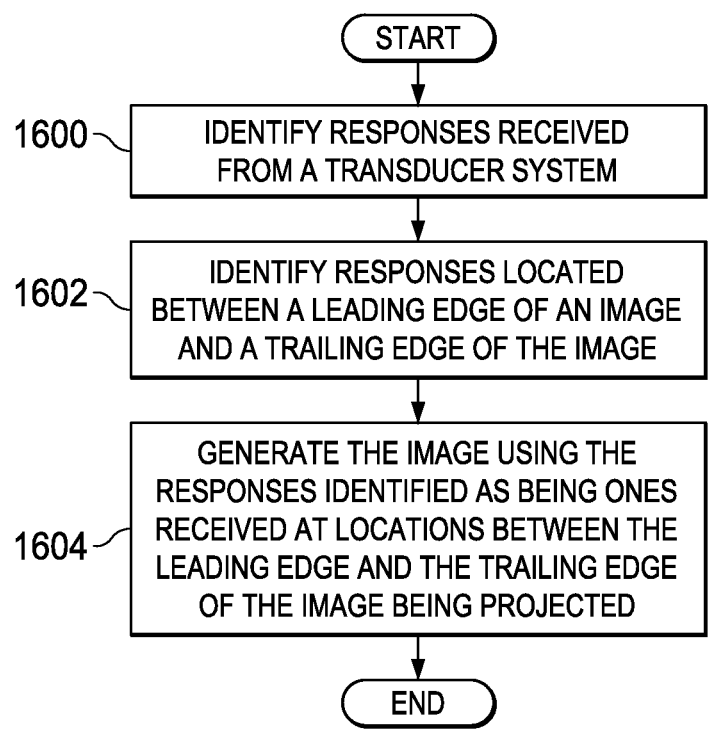
FIG. 16 is an illustration of a flowchart of a process for generating an image in accordance with an illustrative embodiment.

Turning now to FIG. 16, an illustration of a flowchart of a process for generating an image is depicted in accordance with an illustrative embodiment. The process illustrated in FIG. 16 is an example of one manner in which operation 1504 in FIG. 15 may be implemented.

The process begins by identifying responses received from a transducer system (operation 1600). The different responses are associated with location information. For example, each response may be associated with a distance moved by the ultrasonic inspection system from a start point.

The process then identifies responses located between a leading edge of an image and a trailing edge of the image (operation 1602). These responses are ones that were received at locations having a distance that is greater than the offset of the transducer array to the leading edge of the image. The responses are also ones received at locations having a distance less than the length from the leading edge to the trailing edge of the image. In other words, an inconsistency displayed in the image moves toward the trailing edge of the image as the transducer array moves away from the inconsistency.

The signals from the array of transducers take the form of lines of data. The lines of data are gathered sequentially as the transducer system moves forward. These lines of data may be used to form C-scan data. The C-scan data may be used to form an image. This image is a two-dimensional depiction of the surface being scanned. Typically, reversal of the movement of the transducer system is detected by the encoder, and sequential lines of data are gathered in reverse sequence, overwriting those lines of data that were gathered before at the same x-axis positions while travelling in the forward direction.

The process then generates the image using the responses identified as being ones received at locations between the leading edge and the trailing edge of the image being projected (operation 1604), with the process terminating thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 17:
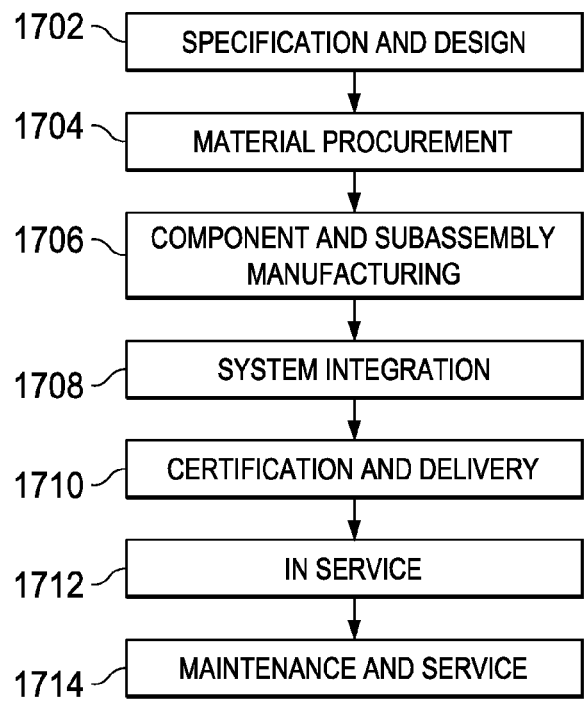
FIG. 17 is an illustration of an aircraft manufacturing and service method in accordance with an illustrative embodiment.
Figure 18:
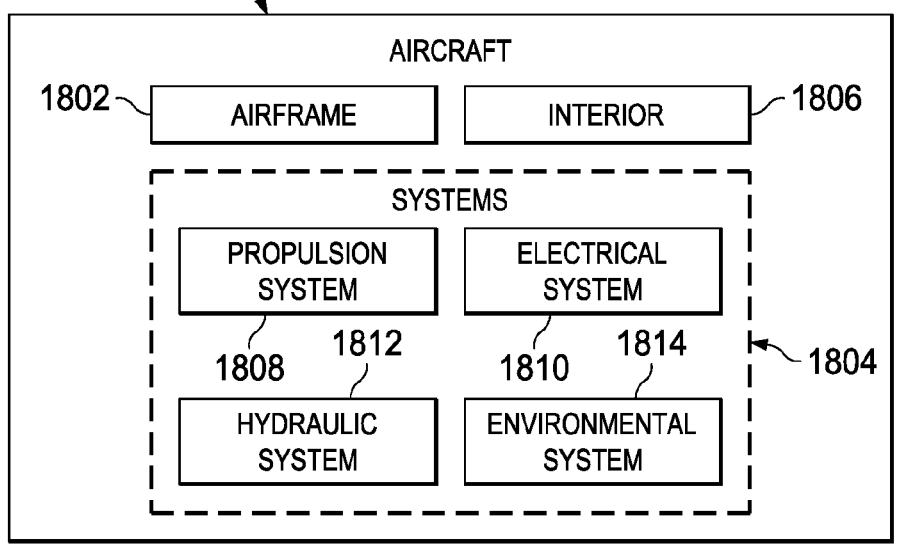
FIG. 18 is an illustration of an aircraft in which an illustrative embodiment may be implemented.

Illustrative embodiments of the disclosure may be described in the context of aircraft manufacturing and service method 1700 as shown in FIG. 17 and aircraft 1800 as shown in FIG. 18. Turning first to FIG. 17, an illustration of an aircraft manufacturing and service method is depicted in accordance with an illustrative embodiment. During pre-production, aircraft manufacturing and service method 1700 may include specification and design 1702 of aircraft 1800 in FIG. 18 and material procurement 1704.

During production, component and subassembly manufacturing 1706 and system integration 1708 of aircraft 1800 takes place. Thereafter, aircraft 1800 may go through certification and delivery 1710 in order to be placed in service 1712. While in service 1712 by a customer, aircraft 1800 in FIG. 18 is scheduled for routine maintenance and service 1714, which may include modification, reconfiguration, refurbishment, and other maintenance or service.

Each of the processes of aircraft manufacturing and service method 1700 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 18, an illustration of an aircraft is depicted in which an illustrative embodiment may be implemented. In this example, aircraft 1800 is produced by aircraft manufacturing and service method 1700 in FIG. 17 and may include airframe 1802 with plurality of systems 1804 and interior 1806. Examples of systems 1804 include one or more of propulsion system 1808, electrical system 1810, hydraulic system 1812, and environmental system 1814. Any number of other systems may be included. Although an aerospace example is shown, different illustrative embodiments may be applied to other industries, such as the automotive or boating industry.

Apparatuses and methods embodied herein may be employed during at least one of the stages of aircraft manufacturing and service method 1700 in FIG. 17. In particular, one or more illustrative embodiments may be used to perform inspections of structures for aircraft 1800.

In one illustrative example, components or subassemblies produced in component and subassembly manufacturing 1706 in FIG. 17 may be fabricated or manufactured in a manner similar to components or subassemblies produced while aircraft 1800 is in service 1712 in FIG. 17. As yet another example, one or more apparatus embodiments, method embodiments, or a combination thereof may be utilized during production stages, such as component and subassembly manufacturing 1706 and system integration 1708 in FIG. 17. For example, structures such as skin panels, joints, fuselage sections, and other components may be inspected using ultrasonic inspection system 202 in FIG. 2 manufactured during component and subassembly manufacturing 1706 and as assembled during system integration 1708.

One or more apparatus embodiments, method embodiments, or a combination thereof may be utilized while aircraft 1800 is in service 1712 and/or during maintenance and service 1714 in FIG. 17. For example, ultrasonic inspection system 900 in FIG. 9 may be used to inspect various portions of aircraft 1800 during maintenance and service 1714 or while aircraft 1800 is on the ground when in service 1712. The use of a number of the different illustrative embodiments may substantially expedite the assembly of and/or reduce the cost of aircraft 1800.

Thus, the illustrative embodiments provide a method and apparatus for inspecting objects. The inspection of objects may be performed more quickly, with less expense, or both using an illustrative embodiment. The projection of images onto the surface of the object being inspected is such that an inconsistency is indicated in the image at substantially the same location at which the inconsistency was detected in the object. In this manner, an operator may mark inconsistencies more quickly. Additional testing and use of transparencies may be avoided using an illustrative embodiment.

In one illustrative embodiment, the detection and indication of inconsistencies may be made without using other external devices. Also, a coordinate system relative to a reference point in the object is not needed to identify and indicate a presence of inconsistencies.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
    a platform configured to move on a surface of an object;
    a location system for the platform and configured to generate location information for the platform on the surface of the object;
    a transducer system associated with the platform and configured to send signals into the object and receive a response to the signals;
    a projector system associated with the platform and configured to project an image onto the surface of the object; and
    a data processing system in communication with the transducer system and the projector system, wherein the data processing system is configured to:
        generate the image using the response in which an indication of an inconsistency in the image projected onto the surface of the object corresponds to a location of the inconsistency in the object; and
        control the projector system to project the image onto the surface of the object;
    wherein the projector system is attached to the platform.

2. The apparatus of claim 1, wherein the data processing system uses the location information to generate the image with the indication of the inconsistency in the image such that the indication corresponds to the location of the inconsistency in the object when the image is projected onto the surface of the object.

3. The apparatus of claim 1, wherein the location information is a distance moved by the platform.

4. The apparatus of claim 1, wherein the transducer system comprises:
    an array of transducers configured to send the signals into the object and receive the response to the signals.

5. The apparatus of claim 4, wherein the transducer system further comprises:
    a cylindrical housing configured to roll on the surface of the object as the platform moves on the surface of the object, wherein the array of transducers is located within the cylindrical housing.

6. The apparatus of claim 4, wherein the array of transducers comprises:
    an array of piezoelectric transducers.

7. The apparatus of claim 1, wherein at least one of the location system and the data processing system is associated with the platform.

8. The apparatus of claim 1, wherein the location system comprises:
    an encoder system.

9. The apparatus of claim 1, wherein the platform is selected from one of a handheld platform, a portable platform, and a motorized platform.

10. The apparatus of claim 1, wherein the image is a C-scan generated from the response.

11. The apparatus of claim 1, wherein the image has a scale of 1:1.

12. The apparatus of claim 1, wherein the data processing system is configured to generate an alert when a first amplitude in the response is greater than a second amplitude for an absence of the inconsistency by a selected amount.

13. The apparatus of claim 1, wherein the object is selected from one of an aircraft, a mobile platform, a stationary platform, a land-based structure, an aquatic-based structure, a space-based structure, a submarine, a bus, a personnel carrier, a tank, a train, an automobile, a spacecraft, a space station, a satellite, a surface ship, an engine housing, a fuselage, a wing, a composite airfoil, a composite skin panel, a metal skin panel, a vertical stabilizer, a horizontal stabilizer, and a joint.

14. An apparatus comprising:
    a platform configured to move on a surface of an object;
    a location system for the platform and configured to generate location information for the platform on the surface of the object;
    a detection system associated with the platform and configured to generate data about the object;
    a projector system associated with the platform and configured to project an image onto the surface of the object; and
    a data processing system in communication with the detection system and the projector system, wherein the data processing system is configured to:
        generate the image using the data from the detection system in which an indication of an inconsistency in the image projected onto the surface of the object corresponds to a location of the inconsistency in the object; and
        control the projector system to project the image onto the surface of the object;
    wherein the projector system is attached to the platform.

15. The apparatus of claim 14, wherein the detection system is selected from one of a transducer system and an eddy current testing system.

16. A method for indicating an inconsistency, the method comprising:
- generating an image using a response received from signals sent into an object from a transducer system in an ultrasonic inspection system in which an indication of the inconsistency is present in the image; and
- projecting the image onto a surface of the object from a projector in the ultrasonic inspection system such that the indication of the inconsistency in the image corresponds to a location of the inconsistency in the object;
- wherein the projector is attached to a platform of the ultrasonic inspection system; and
- wherein the platform is configured to move on the surface of the object.

17. The method of claim 16 further comprising:
- sending the signals into the object from the transducer system; and
- receiving the response to the signals at the transducer system.

18. The method of claim 16, wherein the image is generated using location information about the ultrasonic inspection system on the surface of the object.

19. The method of claim 16 further comprising:
- adjusting the image in response to movement of the transducer system.

20. The method of claim 16, wherein the object is selected from one of an aircraft, a mobile platform, a stationary platform, a land-based structure, an aquatic-based structure, a space-based structure, a submarine, a bus, a personnel carrier, a tank, a train, an automobile, a spacecraft, a space station, a satellite, a surface ship, an engine housing, a fuselage, a wing, a composite airfoil, a composite skin panel, a metal skin panel, a vertical stabilizer, a horizontal stabilizer, and a joint.

21. The apparatus of claim 1,
- wherein the location system is attached to the platform; and
- wherein the transducer system is attached to the platform.

22. The apparatus of claim 1,
- wherein the data processing system is attached to the platform;
- wherein the platform includes a handle;
- wherein the transducer system takes a form of an array of piezoelectric transducers located inside of a cylindrical housing;
- wherein the cylindrical housing one of rigid or deformable and is comprised of one or more materials that are conducive to transmission of signals generated by the array of piezoelectric transducers within cylindrical housing;
- wherein a coupling fluid is present within the cylindrical housing;
- wherein the cylindrical housing forms a first roller;
- wherein the roller is part of a locomotion system for moving the platform on the surface of the object that is to be inspected;
- wherein the location system comprises an encoder, which includes a second roller;
- wherein the second roller is part of the locomotion system for the platform to aid in moving the platform on the surface of the object;
- wherein the encoder comprises an encoder wheel that is in contact with the second roller, such that as the encoder wheel turns, the location information about a distance traveled by the platform is generated by an encoder circuit attached to the platform;
- wherein the image is displayed with an offset from an array of transducers within the cylindrical housing in the transducer system;
- wherein the offset along with the location information from the location system are used to generate and change the image such that the indication is displayed on the surface of the object in the location corresponding to the inconsistency detected by the apparatus;
- wherein the offset is a distance from the array of transducers in the cylindrical housing to a leading edge of the image;
- wherein the image reflects information generated while the transducer system was located over the inconsistency;
- wherein the indication shifts from the leading edge of the image toward a trailing edge of the image; and
- wherein the inconsistency is displayed at the leading edge after the transducer system is moved a distance corresponding to the offset in a direction from the trailing edge towards the leading edge.

* * * * *